United States Patent [19]

Schellhammer et al.

[11] 4,069,228
[45] Jan. 17, 1978

[54] COUMARINS CONTAINING SULPHONYLAMINO GROUPS

[75] Inventors: Carl Wolfgang Schellhammer; Florin Seng, both of Schildgen, Germany

[73] Assignee: Bayer Aktiengesellschaft, Leverkusen, Germany

[21] Appl. No.: 698,925

[22] Filed: June 23, 1976

[30] Foreign Application Priority Data

June 27, 1975  Germany .............................. 2528698

[51] Int. Cl.$^2$ .................. C07D 405/04; C07D 407/04
[52] U.S. Cl. ........................... 260/308 R; 260/308 B; 260/343.44; 260/343.43; 260/556 C; 544/223; 548/374
[58] Field of Search .................... 260/343.2 R, 310 R, 260/308 A, 308 R, 308 B

[56] References Cited

U.S. PATENT DOCUMENTS

| | | | |
|---|---|---|---|
| 3,156,697 | 11/1964 | Moffett | 260/343.2 R |
| 3,966,755 | 6/1976 | Schläpfer | 260/310 R |

FOREIGN PATENT DOCUMENTS

| | | | |
|---|---|---|---|
| 41-13944 | 4/1969 | Japan | 260/310 R |

OTHER PUBLICATIONS

Alfons et al., Chem. Abs., vol. 77, 1972, pp. 7314d, 7315e.
Carter, Organic Reactions, vol. 3, p. 207, 1962.

*Primary Examiner*—Natalie Trousof
*Assistant Examiner*—Jane T. Fan
*Attorney, Agent, or Firm*—Plumley and Tyner

[57] ABSTRACT

Coumarins of the formula

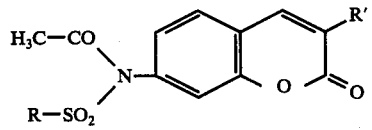

wherein
  R denotes an alkyl radical with 1 to 4 C atoms, which is optionally substituted by halogen atoms or a phenyl radical which is optionally substituted by halogen, $C_1$–$C_4$-alkyl or $C_1$–$C_4$-alkoxy and
  R' represents hydrogen, a phenyl radical which is optionally substituted by nitro, $C_1$–$C_4$alkyl, halogen or $C_1$–$C_4$-alkoxy, the tetralin-6-yl radical or an aromatic heterocyclic radical which is bonded via C or N and which can contain further substituents, for example $C_1$–$C_4$-alkyl groups and halogen atoms
are valuable intermediates for the production of dyestuffs and optical brightening agents.

7 Claims, No Drawings

COUMARINS CONTAINING SULPHONYLAMINO GROUPS

The invention relates to coumarins of the formula

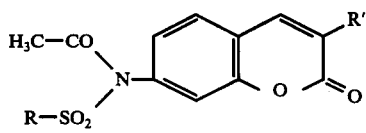
(I)

which are substituted in the 7-position by sulphonylacetylamino, a process for their preparation and their use as intermediates for the preparation of dyestuffs and optical brighteners.

In the formula I R denotes an alkyl radical with 1 to 4 C atoms, which is optionally substituted by halogen atoms or a phenyl radical which is optionally substituted by halogen, $C_1$-$C_4$-alkyl or $C_1$-$C_4$-alkoxy. R' represents hydrogen, a phenyl radical which is optionally substituted by nitro, $C_1$-$C_4$-alkyl, halogen or $C_1$-$C_4$-alkoxy, the tetralin-6-yl radical or an aromatic heterocyclic radical which is bonded via C or N and which can contain further substituents, for example $C_1$-$C_4$-alkyl groups and halogen atoms.

Suitable heterocyclic-aromatic radicals are, for example, the benzofuran-2-yl radical, the 1,2,4-triazol-1-yl radical, the pyrazol-1-yl radical, the 4-chloropyrazol-1-yl radical or the benzotriazol-2-yl radical.

Suitable halogen is, in particular, chlorine.

The compounds according to the invention are obtained when sulphonylaminosalicylaldehydes of the formula

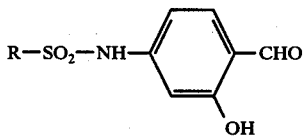
(II)

wherein
R has the abovementioned meaning, are reacted with acetic anhydride, a basic condensing agent and an acetic acid of the formula

R'-CH$_2$-COOH     (III)

wherein
R' has the abovementioned meaning, at temperatures between 100° and 180° C for 3 to 30 hours. If R' represents hydrogen, the addition of the acetic acid can be dispensed with.

Alkali metal acetates, such as sodium acetate or potassium acetate, and tertiary bases such as triethylamine, dimethylbenzylamine, pyridine or acetanilide are used as basic condensing agents. The amount of acetic anhydride must be at least 3 mols per mol sulphonylaminosalicylaldehyde and approximately an excess of between 4 and 10 mols is taken. The reaction temperature can be between 100° and 180° C, approximately between 135° and 150° C. The reaction time varies between 3 and 30 hours and the highest yields are usually obtained after 10 to 15 hours.

For working up, the product which has separated out in the reaction mixture can be filtered off direct and freed from inorganic salts by washing with water. However, it is also possible to decompose the excess acetic anhydride by adding water and a lower alcohol, such as methanol or ethanol, and then to isolate the product. The coumarins of the formula I, which are substituted in the 7-position by sulphonylamino, are obtained in yields of between 60 and 86% of theory by this process.

The products according to the invention are colourless to orange coloured crystals, which are valuable intermediates for the preparation of dyestuffs and optical brighteners.

Compared with the intermediate known hitherto, which have no sulphonyl substituents on the nitrogen atom in the 7-position, the new intermediates are obtained in better yields during preparation of the coumarins and are accessible via a route which does not pass through p-aminosalicylic acid, which has only limited storage stability.

Starting from m-aminophenol, the compounds according to the invention are prepared in accordance with the following reaction equation (a); the process carried out industrially hitherto, (b), is shown alongside for comparison:

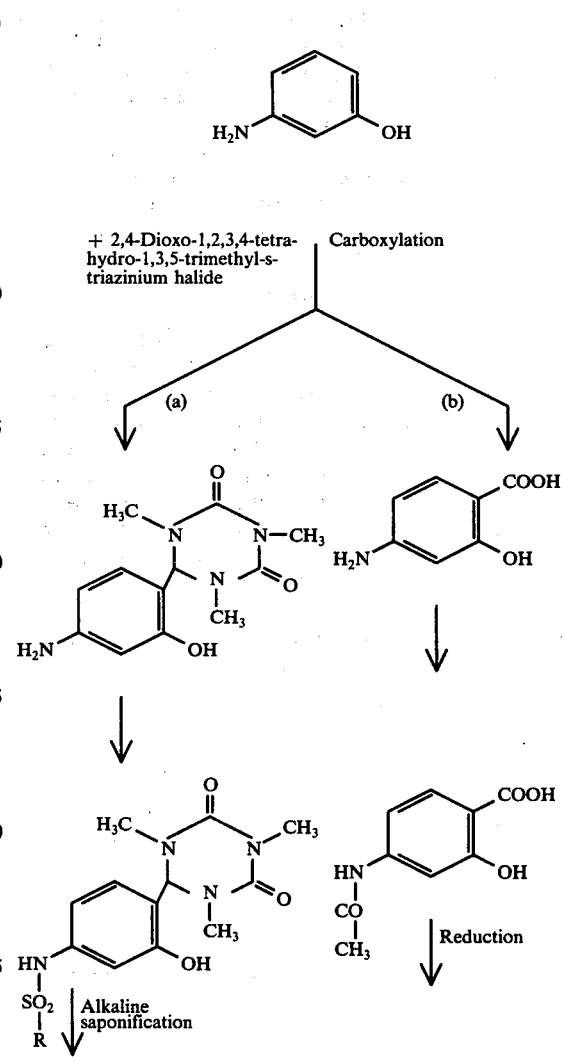

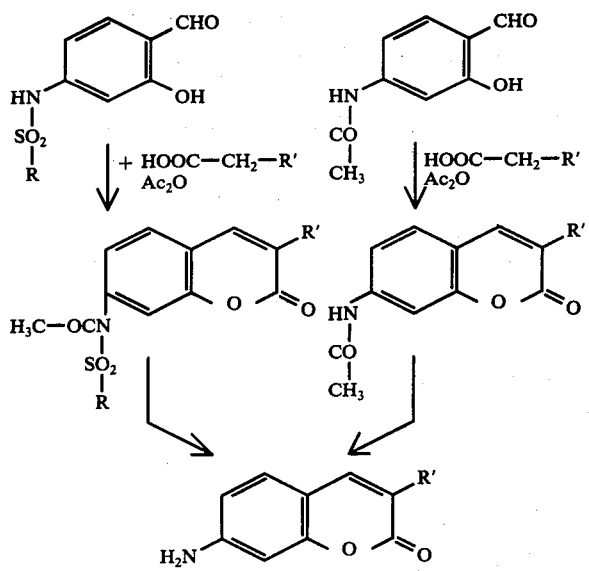

EXAMPLE 1

A mixture of 27.7 g of 4-benzenesulphonamidosalicyl-aldehyde, 51 g of acetic anhydride and 8.2 g of sodium acetate is boiled under reflux for 15 hours. The reaction mixture is them allowed to cooled to 90° C and a mixture of 50 ml of methanol and 50 ml of water is added. Half an hour later, the mixture is cooled to +10° C and the material which has separated out is filtered off and washed with hot water and with methanol. After drying, 23 g of 7-N-acetyl-N-benzenesulphonylaminocoumarin are obtained as brownish crystals. After recrystallisation from glycol monomethyl ether-acetate, the compound forms colourless crystals with a melting point of 201° to 206° C.

EXAMPLE 2

A mixture of 27.7 g of 4-benzenesulphonamidosalicylaldehyde, 9.8 g of anhydrous sodium acetate, 16.3 g of phenylacetic acid and 51 g of acetic anhydride is boiled under reflux for 15 hours. The reaction mixture is then treated, at 90° to 60° C, with 50 ml of methanol, sitrred hot for a further 30 minutes and then cooled. The yield of 7-N-acetyl-N-benzenesulphonylamino-3-phenylcourmarin is 36.1 g of grey crystals, which after recrystallisation from glycol monomethyl ether-acetate give colourless crystals with a melting point of 215° C.

When other acetic acids used in place of phenylacetic acid, the products mentioned in the Table are obtained in similar yields.

Table

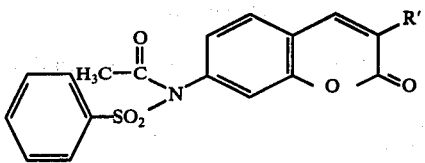

| Acetic acid | R' | Melting point °C |
|---|---|---|
| 4-tert.-Butylphenylacetic acid | 3-(4-tert.-Butyl-phenyl)- | 225 to 227 |
| 4-Methoxyphenyl-acetic acid | 3-(4-Methoxy-phenyl)- | 181 to 183 |
| 3-Chlorophenylacetic acid | 3-(3-Chlorophenyl)- | 188 to 189 |

Table-continued

| Acetic acid | R' | Melting point °C |
|---|---|---|
| 4-Nitrophenylacetic acid | 3-(4-Nitrophenyl)- | 224 to 226 |
| 4-Dimethylaminophenyl-acetic acid | 3-(4-Dimethylamino-phenyl)- | 210 to 212 |
| Tetralin-6-yl-acetic acid | 3-[Tetralin-6-yl]- | 194 to 198 |
| Benzofuran-2-yl-acetic acid | 3-[Benzofuran-2-yl]- | 228 to 230 |
| 4-Chloro-pyrazol-1-yl-acetic acid | 3-[4-Chloropyrazol-1-yl] | 226 to 228 |
| 1,2,4-Triazol-1-yl-acetic acid | 3-[1,2,4-Triazol-1-yl] | 244 to 247 |
| Benzotriazol-2-yl-acetic acid | 3-[Benzotriazol-2-yl] | 230 to 232 |

EXAMPLE 3

A mixture of 8 g of 4-m-chlorobenzenesulphonamidosalicylaldehyde, 3.9 g of 1,2,4-triazol-1yl-acetic acid, 2.5 g of anhydrous sodium acetate and 50 ml of acetic anhydride is boiled under reflux for 15 hours. After working up, which is carried out as in Example 2, 2.3 g of 7-N-acetyl-N-(m-chlorobenzenesulphonyl)-amino-3-[1,2,4-triazol-1-yl]-coumarin of melting point 236° to 237° C (from methylglycol) are obtained.

EXAMPLE 4

10.2 g of 4-p-tolylsulphonamidosalicylaldehyde, 7 g of 4-chloropyrazol-1-yl-acetic acid, 3.5 g of anhydrous sodium acetate and 50 ml of acetic anhydride are boiled under reflux for 15 hours. After the customary working up, 10.3 g of 7-N-acetyl-N-(p-tolylsulphonyl)-amino-3-[4-chloropyrazol-1-yl]-coumarin of melting point 218° to 221° C (from methylglycol) are obtained.

EXAMPLE 5

A mixture of 8.5 g of 4-(o-toluenesulphonamido)-salicylaldehyde, 4.8 g of phenylacetic acid, 2.9 g of anhydrous sodium acetate and 50 ml of acetic anhydride is boiled under reflux for 15 hours. After the customary working up, 6 g of 7-N-acetyl-N-(o-tolylsulphonyl)-amino-3-phenyl-coumarin of melting point 219° to 222° C (from methylglycol) are obtained.

EXAMPLE 6

A mixture of 17.3 g of 4-(3,4-dichlorobenzenesulphonamido)-salicylaldehyde, 7.6 g of 1,2,4-triazol-1-yl-acetic acid, 5 g of sodium acetate and 50 ml of acetic anhydride is boiled under reflux for 15 hours. After the customary working up, 16.8 g of 7-N-acetyl-N-(3,4-dichloro-benzenesulphonyl)-amino-3-[1,2,4-triazol-1-yl]-coumarin of melting point 232° to 235° C (from xylene) are obtained.

EXAMPLE 7

A mixture of 10.8 g of 4-methylsulphonamido-salicylaldehyde, 9.6 g of 4-chloropyrazol-1-yl-acetic acid, 7.6 g of anhydrous sodium acetate and 50 ml of acetic anhydride is boiled under reflux for 15 hours. After the customary working up, 11.5 g of 7-N-acetyl-N-methylsulphonylamino-3-[4-chloro-pyrazol-1-yl]-courmarin of melting point 209°–212° (from xylene) are obtained.

The sulphonylamino-substituted salicylaldehydes are obtained, for example, as follows.

EXAMPLE 8

2,4-Dioxo-hexahydro-1,3,5-trimethyl-s-triazine 145 g (1 mol) of 1,3,5-trimethyl-biuret and 30 g of paraformaldehyde are heated together with 5 ml of concentrated hydrochloric acid 70° C for 5 hours. The liquid contents of the flask are then poured onto a dry metal sheet and, after solidification, the product is re-crystallised from cyclohexane. This gives 145 g (98%) of 2,4-dioxo-hexahydro-1,3,5-trimethyl-s-triazine of melting point 88° to 90° C.

EXAMPLE 9

2,4-Dioxo-1,2,3,4-tetrahydro-1,3,5-trimethyl-s-triazinium bromide 15.7 g (0.1 mol) of 2,4-dioxo-hexahydro-1,3,5-trimethyl-s-triazine are dissolved in 30 ml of methylene chloride and 24 g (0.15 mol) of bromine are added dropwise, whilst the temperature is kept between 20° and 30° C by cooling. After a few minutes 2,4-dioxo-1,2,3,4-tetrahydro-1,3,5-trimethyl-s-triazinium bromide separates out in the form of orange coloured crystals. These are filtered off and recrystallised from isopropanol. This gives 20 g (85%) of 2,4-dioxo-1,2,3,4-tetrahydro-1,3,5-trimethyl-s-triazinium bromide as white crystals which melt at 217° C.

EXAMPLE 10

2,4-Dioxo-hexahydro-1,3,5-trimethyl-6-[2-hydroxy-4-aminophenyl]-s-triazine

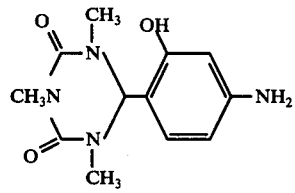

23.6 g (0.1 mol) of 2,4-dioxo-1,2,3,4-tetrahydro-1,3,5-trimethyl-s-triazinium bromide are dissolved in 50 ml of water and 10.9 g (0.1 mol) of m-aminophenol are added. A clear solution has formed after a few minutes. 8 g of sodium bicarbonate are added to the solution. Hereupon 25 g (89%) of 2,4-dioxo-hexahydro-1,3,5-trimethyl-6-[2-hydroxy-4-aminophenyl]-s-triazine are precipitated as white crystals, which, after dissolving in aqueous hydrochloric acid and clarifying the solution with active charcoal and neutralising, melt at 240° C.

EXAMPLE 11

4-Benzenesulphonamido-salicylaldehyde 432 g (1 mol) of 2,4-dioxo-hexahydro-1,3,5-trimethyl-6-[2-hydroxy-4-benzenesulphonamido-phenyl]-s-triazine (93.5% pure product) are introduced into a solution of 280 g (7 mols) of sodium hydroxide in 600 ml of water. The mixture is boiled under reflux and under nitrogen for 6 hours. A pale brown solution is formed, from which small single crystals separate out. The contents of the flask are then poured onto a mixture of 700 ml of concentrated hydrochloric acid and 2 kg of ice and the yellow product which has separated out is filtered off. After washing with water and drying at 80° C, 274 g of 4-benzene-sulphonamido-salicylaldehyde of melting point 150° to 157° C are obtained. According to the oxime titration, the aldehyde is 94.8% pure and the yield is thus 93.6%. After recrystllisation from xylene (1 : 10), the aldehyde is obtained as colourless crystals of melting point 160° to 163° C.

The products according to the invention are, for example, further processed as follows to give optical brighteners.

EXAMPLE 12

7-Hydrazino-3-[1,2,4-triazol-1-yl]-coumarin 86.4 g (0.2 mol) of 7-(N-acetyl-N-benzenesulphonyl-)amino-3-[1,2,4-triazol-1-yl]-coumarin (94.2% pure crude product) in 80 ml of 80% strength sulphuric acid were stirred for 3 hours at 100° C. 1 g of KCl is then added and 0.2 mol of nitrosylsulphuric acid is added dropwise at 10° to 15° C. The contents of the flask are discharged onto 400 g of ice and the dark solution thus obtained is added dropwise at 2° to 5° C in the course of 20 minutes to 193 ml of 40% strength sodium bisulphite solution. After 3 hours, the material which has separated out is filtered off, washed with saturated sodium chloride solution and stirred with 185 ml of 37% strength hydrochloric acid for 4-5 hours at 65° C. The mixture is then cooled to 15° C and the material which has separated out is filtered off and washed with saturated sodium chloride solution. The filter cake is stirred into 200 ml of hot water; the pH is adjusted to 5.5 with 45% strength sodium hydroxide solution, the mixture is stirred for a further 2 hours and the product is filtered off, washed with water and dried. The yield is 35.3 g of 7-hydrazino-3-[1,2,4-triazol-1-yl]-coumarin, which, when introduced into a molten state reaction apparatus preheated to 240° C, adds itself at 255° to 257° C.

The compound can be used to prepare 7-[3-methyl-pyrazol-1-yl]-3-[4-methyl-1,2,4-triazolium-1]-coumarin methosulphate according to U.S. Patent Specification 3,663,560, Example 1, or 7-[4-ethyl-5-methyl-1,2,3-triazol-2-yl]-3-[4-methyl-1,2,4-triazolium-1]-coumarin methosulphate according to British Patent Specification 1,201,759.

We claim:

1. A coumarin of the formula

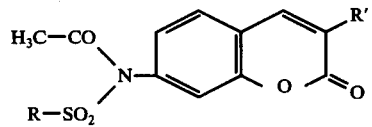

wherein
R is $C_1$-$C_4$-alkyl unsubstituted or substituted with halogen; or phenyl unsubstituted or substituted with halogen, $C_1$-$C_4$-alkyl, or $C_1$-$C_4$-alkoxy; and
R' is an aromatic heterocyclic radical selected from the group consisting of benzofuran-2-yl, 1,2,4-triazol-1-yl, pyrazol-1-yl, 4-chloropyrazol-1-yl and benzotriazol-2-yl, each of which is unsubstituted or subtituted with $C_1$-$C_4$-alkyl or halogen.

2. The compound of claim 1 wherein R is phenyl and R' is 3-[4-chloropyrazol-1-yl].

3. The compound of claim 1, wherein R' is benzofuran-2-yl, 1,2,4-triazol-1-yl, pyrazol-1-yl or benzotriazol-2-yl, each of which is unsubstituted or substituted with $C_1$-$C_4$-alkyl or halogen.

4. The compound of claim 1, wherein R is phenyl and R' is 3-[1,2,4-triazol-1-yl].

5. The compound of claim 1, wherein R is phenyl and R' is 3-[benzotriazol-2-yl].

6. The compound of claim 1, wherein R is phenyl and R' is 3-[benzofuranyl-2-yl].

7. The compound of claim 1, wherein R is methyl and R' is 3-[4-chloropyrazol-1-yl].

* * * * *